US008292915B2

(12) United States Patent
Akcasu

(10) Patent No.: US 8,292,915 B2
(45) Date of Patent: Oct. 23, 2012

(54) HAND-HELD ACUPRESSURE DEVICE

(76) Inventor: Feza Akcasu, Burbank, CA (US)

( * ) Notice: Subject to any disclaimer, the term of this patent is extended or adjusted under 35 U.S.C. 154(b) by 599 days.

(21) Appl. No.: 12/392,113

(22) Filed: Feb. 25, 2009

(65) Prior Publication Data

US 2010/0094333 A1 Apr. 15, 2010

Related U.S. Application Data

(60) Provisional application No. 61/031,232, filed on Feb. 25, 2008.

(51) Int. Cl.
*A61B 17/00* (2006.01)

(52) U.S. Cl. ........................................................ 606/204

(58) Field of Classification Search .................. 606/204; 601/63, 80, 134–138, 129, 112–113, 118–119; 446/71, 73, 473, 486, 487; 482/44, 49
See application file for complete search history.

(56) References Cited

U.S. PATENT DOCUMENTS

| | | | | |
|---|---|---|---|---|
| 4,493,315 | A | 1/1985 | Iwahashi | |
| 4,944,747 | A | 7/1990 | Newth et al. | |
| 5,560,746 | A | 10/1996 | Willow | |
| 5,730,708 | A | 3/1998 | Spratt | |
| 6,241,693 | B1 | 6/2001 | Lambden | |
| 6,988,997 | B2 | 1/2006 | Stultz | |
| 7,214,205 | B2 | 5/2007 | Sils | |
| 2003/0009118 | A1 * | 1/2003 | Sabo et al. | 601/137 |
| 2003/0144616 | A1 | 7/2003 | Henderson | |
| 2006/0035751 | A1 * | 2/2006 | Blair et al. | 482/49 |

FOREIGN PATENT DOCUMENTS

JP 2006305112 A * 11/2006

* cited by examiner

*Primary Examiner* — Elizabeth Houston
*Assistant Examiner* — Anh Dang
(74) *Attorney, Agent, or Firm* — David S. Nagy

(57) ABSTRACT

A hand-held acupressure device which includes a ball attached to an elongated rigid handle by an elastic cord enabling the user to easily position the ball over trigger points. Pressure is applied to the trigger points by pressing the body to the ball against a hard surface. The elastic cord allows the ball freedom of movement apart from the handle while in use, and pulls the ball back to its original position at the end of the handle after use.

5 Claims, 2 Drawing Sheets

HAND-HELD ACUPRESSURE DEVICE

RELATED APPLICATIONS

This application relates to Provisional Patent Application No. 61031232 filed Feb. 25, 2008 entitled "Hand-held Accupressure device."

CROSS-REFERENCE TO RELATED APPLICATIONS

None

FEDERALLY SPONSORED RESEARCH

None

SEQUENCE LISTING

None

FIELD OF THE INVENTION

The present invention in its first embodiment relates to self-operated acupressure devices to release muscle tension in the back and other body areas.

BACKGROUND OF THE INVENTION

Muscle tension, especially in the back and shoulders, is a common problem which often manifests itself through localized spasms of muscle tissue—commonly referred to as "knots" or simply pressure points—throughout the affected muscle. One way of relieving muscle tension is through acupressure whereby pressure is applied onto the knots and maintained for a short period of time, until the spasm releases its tension thereby relaxing the muscle and alleviating the pain and stiffness. Often, multiple applications of acupressure are required to achieve the desired result of tension release. The pressure on the muscle can be applied by pressing fingers, knuckles, or other body parts to the knotted muscle, a practice employed by massage therapists of various disciplines and backgrounds. The difficulty of reaching the areas of one's own back, and other areas of the body, with one's own hands and fingers often makes self-application of acupressure difficult. Even if the acupressure points can be reached with one's hands or fingers, it is often difficult to apply sufficient pressure for the necessary duration. A variety of devices have been developed to address this need.

For instance, the following patents

U.S. Pat. No. 4,493,315 issued to Iwahashi

U.S. Pat. No. 4,944,747 issued to newth et al.

U.S. Pat. No. 5,560,746 issued to Willow

U.S. Pat. No. 5,730,708 issued to Spratt

U.S. Pat. No. 6,241,693 issued to Lambden

U.S. Pat. No. 6,988,997 issued to Stultz present devices with one or two rounded or spheroidal parts of various densities attached to one or two long handles. By means of the handle(s) the rounded surfaces are positioned over the affected areas and pressure or massaging motions are then applied by pulling on the handle(s). Among the drawbacks of this approach is the bulkiness of the apparatus and the fact that the muscle pain and stiffness one desires to relieve will in many cases preclude the arm movements and arm strength necessary to use these devices effectively.

Another approach is demonstrated by U.S. Pat. No. 7,214,205 B2 issued to Sils, and U.S. Patent Application Publication No. US2003/0144616 A1, which employs balls of different densities. The ball(s) are sandwiched between the body and a hard surface (wall, floor, seat, etc.) and pressure is applied by gravity through the modulation of one's body weight. The drawback of this approach is the difficulty of positioning free-rolling balls over the acupressure points which easily shift and slide away under applied external pressure. Positioning and re-positioning these devices can be a major challenge for those with back, neck, and shoulder muscle spasms whose range of motion is often limited.

Therefore, there is a need of a compact, portable hand-held acupressure device which combines the capabilities of easy positioning and re-positioning that attached handles provide, with the positive attributes that free-rolling balls provide: the easily achieved minor positional adjustments, the portability, and the utilization of one's body weight to apply the necessary pressure to achieve targeted muscle-tension release for the reduction of pain and stiffness. In addition, there is a need for a hand-held acupressure device which is conveniently portable for use in a variety of environments that is relatively simple in construction, durable, and relatively inexpensive to manufacture.

SUMMARY

The object of this first embodiment is to remedy the abovementioned limitations of existing hand-held acupressure devices while combining their respective advantages. This embodiment combines the ease of use, portability, and simplicity of using a free-rolling ball as a means of applying acupressure to targeted muscle spasms with the positioning advantages an attached handle provides. This embodiment accomplishes this by attaching a semi-rigid ball to a rigid tube by means of an elastic cord with sufficient tension so that the ball and handle behave as essentially a one-piece unit easily positioned over even hard-to-reach areas of the body, yet once sandwiched between the body and a hard surface, the cord's elasticity enables the ball to freely-roll in all directions over a limited yet completely sufficient distance for the purpose of effectively applying pressure onto the various acupressure points. When the body's weight is released from the ball, the elastic cord pulls it back into place at the end of the handle whereby handle and ball return to its single-piece configuration.

DRAWINGS

REFERENCE NUMERALS

11 ball

12 handle 13 end cap
14 elastic cord
15 retaining washer (in handle)
16 cord end (in handle)
17 guide washer
18 retaining washer (in ball)
19 cord end (in ball)

DETAILED DESCRIPTION OF THE FIRST EMBODIMENT

Figure 1:
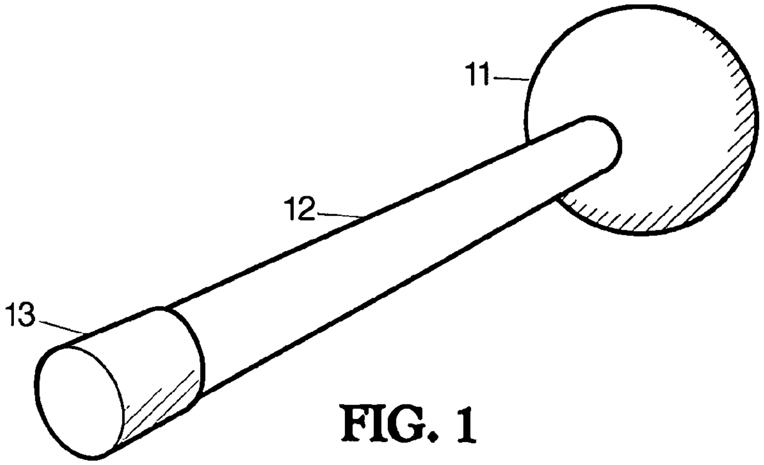
FIG. 1 is a perspective view from the right rear of this first embodiment of the hand-held acupressure device from the back end of the handle looking towards the front end where the attached ball is situated.

FIG. 1 shows the first embodiment of the hand-held acupressure device which incorporates a ball 11 attached to a handle 12 in perspective. The ball 11 can be a hollow, rubber ball or other semi-rigid spheroid of approximate size, shape, and properties of a generic tennis ball, but not necessarily limited to these specifications. The handle 12 is a rigid, round, hollow tube with an outer diameter of approximately three-quarters of an inch and a length of approximately 18 inches in the present embodiment, though other diameters, lengths, and cross-sections are suitable, made of hard plastic or other similar material. An end cap 13 of soft plastic or similar material covers the end of the handle 12 opposite where ball 11 is situated and is used for aesthetic purposes to give the device a more finished look.

Figure 2:
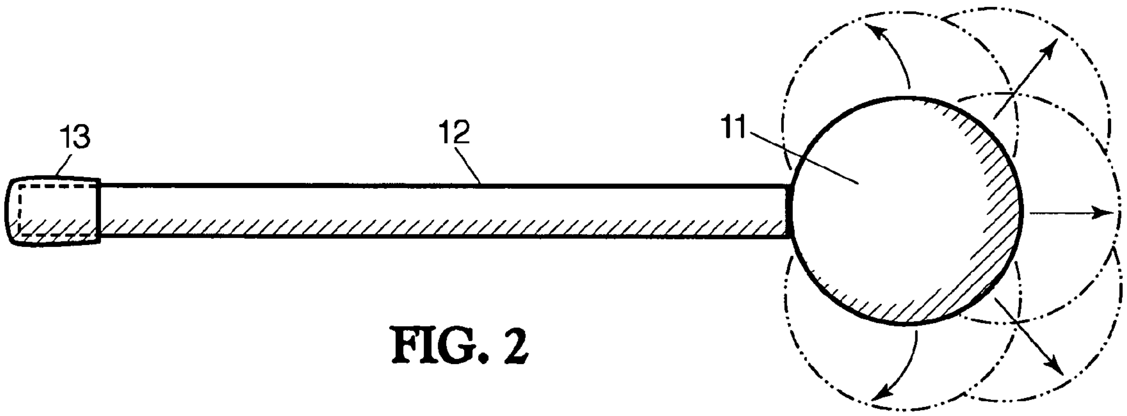
FIG. 2 is a side view of the hand-held acupressure device indicating the variable positions through movement of the attached ball.

FIG. 2 shows a side view of this embodiment with end cap 13 fitting over the back end of handle 12. Also depicted, is an indication of the various possible positions and movements ball 11 is capable of implementing respective to, and independent of, handle 12. Though only the movement in two-dimensions is depicted for visual clarity, ball 11 achieves omni-directional, three-dimensional movement in practice.

Figure 3:
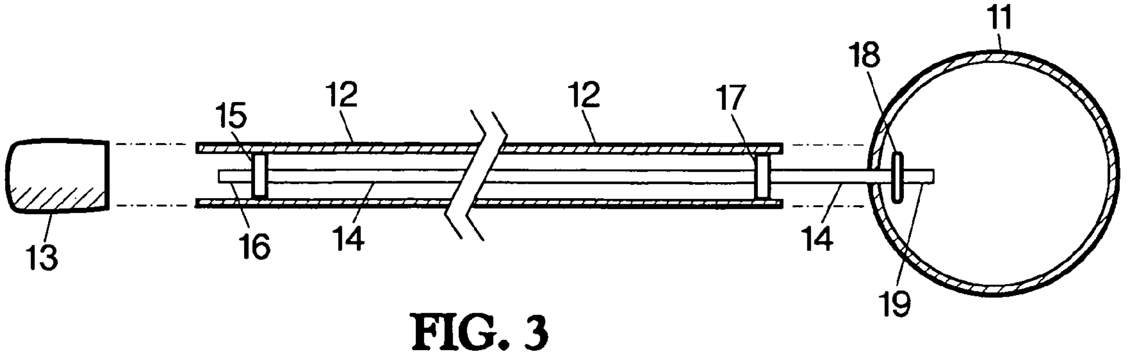
FIG. 3 is an exploded, cross-sectional side view of this embodiment of the hand-held acupressure device.

FIG. 3 is an exploded, cross-sectional view of this first embodiment demonstrating the manner in which ball 11 is attached to handle 12 by an elastic cord 14, having similar properties to what is commonly known as "shock" cord, approximately one-quarter inch in diameter, though other diameters and other materials with similar properties would be suitable, running longitudinally through the hollow tube of handle 12. The elastic cord 14, is anchored to the rear end of handle 12 by way of cord end 16 captured by retaining washer 15 which is permanently affixed to the inside of handle 12.

In addition, FIG. 3 also depicts the other end of handle 12 with elastic cord 14 passing out the other end of handle 12 by freely passing through a guide washer 17 which is permanently affixed to the inside of handle 12. Elastic cord 14 is anchored to the ball by way of cord end 19 being permanently captured by retaining washer 18. This method of anchoring the two ends of elastic cord 14, thus attaching handle 12 to ball 11 specifically refers to this first embodiment of the hand-held acupressure device as depicted, though other methods and materials for attaching the cord end 16 to retaining washer 15 and attaching cord end 19 to retaining washer 18 would be suitable.

Operation

Figure 4:
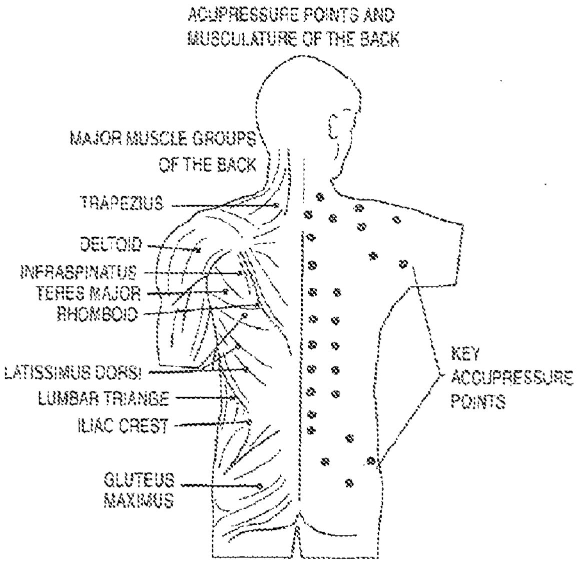
FIG. 4 shows the musculature and acupressure points of the human back.

FIG. 4 shows a human's back musculature and main back acupressure points, though acupressure points for other muscles can be found throughout the body. It is the back muscle groups and pressure points that are the primary targets of this invention as discomfort in this area of the body is most common and most difficult to relieve, though this device in this first embodiment works equally well on all pressure points.

Figure 5A:
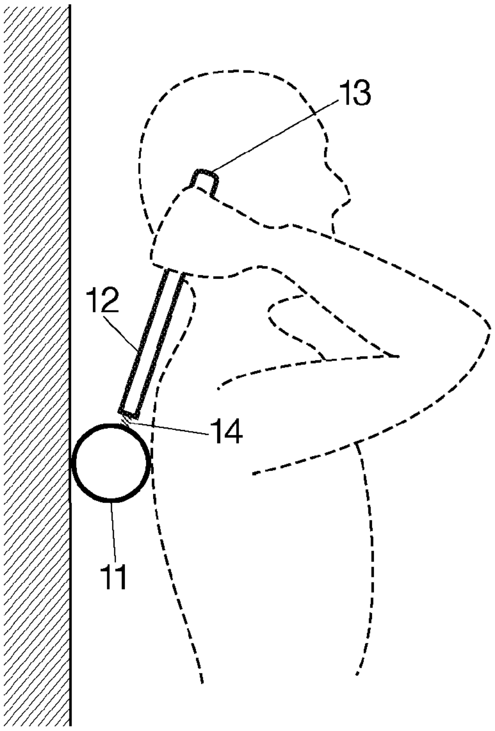
FIGS. 5A and 5B shows two of many various possible methods of holding and positioning the this embodiment of the hand-held acupressure device on the body and its method of use against a hard, vertical, surface, in this case a wall.
Figure 5B:
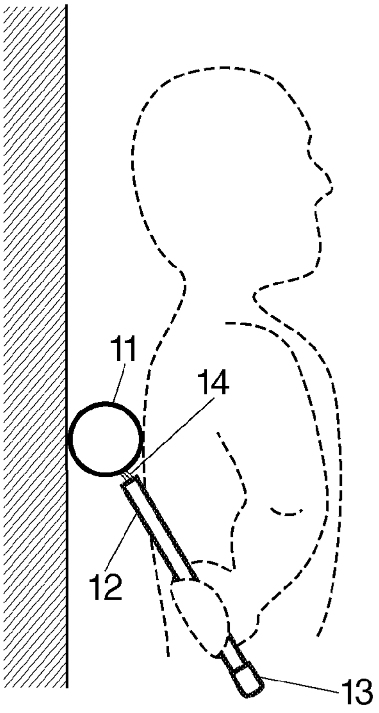

This hand-held acupressure device is used by grabbing hold of handle 12 in either hand, while standing near, lying on, or leaning against, a hard surface such as a wall, floor, or some form of seat back, and positioning ball 11 to the target area (usually being, but not limited to, the hard-to-reach areas of the back musculature). FIG. 5A and FIG. 5B display two methods, out of many alternatives, of positioning this embodiment of the device, in this case against a wall. (Notice that handle 12 enables the positioning of ball 11 from many more angles than is available with free-rolling balls.) Once ball 11 has been primarily positioned, centered on a specific pressure point, the user leans against or lies upon the ball letting their body weight rest against the ball. The goal here is to maintain static pressure on the acupressure point and try to "relax into" the ball which is the desired effect resulting from the muscle spasm eventually relaxing and accepting the pressure applied by ball 11 rather than opposing it with muscle tightness and rigidity. As acupressure points can be very sensitive, the applied pressure can be modulated by slight shifts of the body, one way or another. Minor position adjustments of ball 11, to keep it centered on shifting pressure points, are also made in this manner.

Once the user pins the ball 11 against a hard surface, slightly pulling on handle 12 stretches the elastic cord 14 enabling the ball 11 to move independently from handle 12 and free-rolling, in all directions, over a limited yet very effective distance, a departure from other handle-mounted devices. When the user wants to reposition the ball 11 to a different target area, or when finished, removing the body weight upon ball 11 effectively "un-pins" it enabling the tension of elastic cord 14 to pull ball 11 back to its original position at the end of the handle 12. The beneficial convenience and control this offers persons suffering from muscle spasms and resulting pain and stiffness is immeasurable.

The user can modulate the applied pressure by choosing between vertical and horizontal various hard surfaces depending on what portion of body weight one wants to apply to the pressure point. The compact, simple, portable, configuration of this first embodiment of this invention also lends itself to use in cars against car seats, airplanes against airplane seats, and in trucks and other vehicles, offering more options for relieving muscle tension, pain, and stiffness than just relying on the availability of walls and floors.

The principles and manner of use of this first embodiment of the present invention have been described in the foregoing specification. However, the invention which is intended to be protected is not to be construed as limited to the particulars of the embodiment described. Further, the embodiment described herein is to be regarded as illustrative rather than restrictive. Variations, modifications, and alterations from the present invention may be contemplated by those skilled in the art without departing from the intended spirit and scope of the invention. Accordingly, it is expressly intended that all such variations, changes and equivalents which fall within the spirit and scope of the invention be embraced thereby.

I claim:

1. A hand-held acupressure device for releasing muscle tension, comprising:
 a) a ball to apply pressure to targeted body areas, and
 b) an elongated handle having proximate and distal ends in relation to the ball, and
 c) a stretchable elastic connecting means having two ends connecting said ball to the proximate end of said handle, wherein in an original position the ball is flush against the proximate end of said handle, whereby said handle provides accurate positioning of said ball against targeted body areas, and said stretchable elastic connecting means provides said ball with free and independent movement apart from the proximate end of said handle, and said stretchable elastic connecting means is a means for returning said ball to its original position flush up against the proximate end of said handle.

2. The hand-held acupressure device of claim 1, wherein said ball is a rounded, semi-rigid object of predetermined size, texture, and hardness.

3. The hand-held acupressure device of claim 1, wherein said elongated handle is made of rigid hollow tubing of predetermined length, width, cross-section, and composition.

4. The hand-held acupressure device of claim 1, wherein said stretchable elastic connecting means is of predetermined cross-section thickness and composition to provide attachment of predetermined tension and elasticity between said ball and said elongated handle.

5. The hand-held acupressure device of claim 3, wherein one end of said stretchable elastic connecting means is attached to the inside of said elongated handle somewhere between its proximate and distal ends and runs longitudinally inside said elongated handle and out the proximate end where it is attached to said ball.

* * * * *